(12) United States Patent
Aldridge et al.

(10) Patent No.: US 10,121,557 B2
(45) Date of Patent: Nov. 6, 2018

(54) SYSTEM AND METHOD FOR DYNAMIC DOCUMENT MATCHING AND MERGING

(71) Applicant: PokitDok, Inc., San Mateo, CA (US)

(72) Inventors: Matthew Lee Aldridge, San Mateo, CA (US); Jeffrey Scott Hoekman, San Mateo, CA (US); Colin Erik Alstad, San Mateo, CA (US); Theodore Calhoun Tanner, Jr., San Mateo, CA (US)

(73) Assignee: PokitDok, Inc., San Mateo, CA (US)

( * ) Notice: Subject to any disclaimer, the term of this patent is extended or adjusted under 35 U.S.C. 154(b) by 113 days.

(21) Appl. No.: 14/466,909

(22) Filed: Aug. 22, 2014

(65) Prior Publication Data

US 2015/0205846 A1 Jul. 23, 2015

Related U.S. Application Data

(60) Provisional application No. 61/929,787, filed on Jan. 21, 2014.

(51) Int. Cl.
*G06F 17/30* (2006.01)
*G16H 10/60* (2018.01)
*G06F 19/00* (2018.01)

(52) U.S. Cl.
CPC .......... *G16H 10/60* (2018.01); *G06F 19/322* (2013.01)

(58) Field of Classification Search
CPC .............................. G06F 19/322; G06F 9/4443
See application file for complete search history.

(56) References Cited

U.S. PATENT DOCUMENTS

| | | | |
|---|---|---|---|
| 5,872,021 A | * | 2/1999 | Matsumoto ......... H01L 27/1244 257/E27.111 |
| 6,546,428 B2 | | 4/2003 | Baber et al. |
| 7,386,565 B1 | | 6/2008 | Singh et al. |
| 7,917,378 B2 | | 3/2011 | Fitzgerald et al. |
| 7,917,515 B1 | | 3/2011 | Lemoine |
| 7,970,802 B2 | | 6/2011 | Ishizaki |
| 7,992,153 B2 | | 8/2011 | Ban |
| 8,073,801 B1 | | 12/2011 | Von Halle et al. |
| 8,095,975 B2 | | 1/2012 | Boss et al. |
| 8,103,667 B2 | | 1/2012 | Azar et al. |
| 8,103,952 B2 | | 1/2012 | Hopp |
| 8,203,562 B1 | | 6/2012 | Alben et al. |
| 8,229,808 B1 | | 7/2012 | Heit |
| 8,286,191 B2 | | 10/2012 | Amini et al. |
| 8,359,298 B2 | | 1/2013 | Schacher et al. |

(Continued)

FOREIGN PATENT DOCUMENTS

| | | |
|---|---|---|
| GB | 2478440 | 10/2013 |
| WO | WO 2012/122065 | 9/2012 |

OTHER PUBLICATIONS

Ahlswede et al., *Network Information Flow*, IEEE Transactions on Information Theory, vol. 46, No. 4; Jul. 2000 (13 pgs.).

(Continued)

*Primary Examiner* — Jean M Corrielus
(74) *Attorney, Agent, or Firm* — DLA Piper, LLP (US)

(57) ABSTRACT

A system and method for matching and merging documents from disparate data sources into a single data store for a particular entity are provided. The system and method may be particularly useful for a healthcare system to match and merge data from disparate data sources about a healthcare provider.

17 Claims, 8 Drawing Sheets

(56) References Cited

U.S. PATENT DOCUMENTS

| | | | |
|---|---|---|---|
| 8,364,501 B2 | 1/2013 | Rana et al. | |
| 8,417,755 B1 | 4/2013 | Zimmer | |
| 8,495,108 B2 | 7/2013 | Nagpal et al. | |
| 8,515,777 B1 | 8/2013 | Rajasenan | |
| 8,527,522 B2* | 9/2013 | Baron | G06F 17/3071 707/749 |
| 8,817,665 B2 | 8/2014 | Thubert et al. | |
| 8,984,464 B1 | 3/2015 | Mihal et al. | |
| 9,165,045 B2* | 10/2015 | Mok | G06F 19/322 |
| 9,208,284 B1 | 12/2015 | Douglass | |
| 2002/0022973 A1 | 2/2002 | Sun et al. | |
| 2002/0038233 A1 | 3/2002 | Shubov et al. | |
| 2002/0165738 A1 | 11/2002 | Dang | |
| 2003/0055668 A1 | 3/2003 | Saran et al. | |
| 2003/0097359 A1 | 5/2003 | Ruediger | |
| 2003/0171953 A1 | 9/2003 | Narayanan et al. | |
| 2003/0217159 A1 | 11/2003 | Schramm-Apple et al. | |
| 2003/0233252 A1 | 12/2003 | Haskell et al. | |
| 2004/0143446 A1 | 7/2004 | Lawrence | |
| 2005/0010452 A1 | 1/2005 | Lusen | |
| 2005/0071189 A1 | 3/2005 | Blake et al. | |
| 2005/0102170 A1 | 5/2005 | Lefever et al. | |
| 2005/0137912 A1 | 6/2005 | Rao et al. | |
| 2005/0152520 A1 | 7/2005 | Logue | |
| 2005/0182780 A1 | 8/2005 | Forman et al. | |
| 2005/0222912 A1 | 10/2005 | Chambers | |
| 2006/0036478 A1 | 2/2006 | Aleynikov et al. | |
| 2006/0074290 A1 | 4/2006 | Chen et al. | |
| 2006/0089862 A1 | 4/2006 | Anandarao et al. | |
| 2006/0129428 A1 | 6/2006 | Wennberg | |
| 2006/0136264 A1 | 6/2006 | Eaton et al. | |
| 2007/0113172 A1 | 5/2007 | Behrens | |
| 2007/0118399 A1* | 5/2007 | Avinash | G06F 19/322 705/2 |
| 2007/0156455 A1 | 7/2007 | Tarino et al. | |
| 2007/0174101 A1 | 7/2007 | Li et al. | |
| 2007/0180451 A1 | 8/2007 | Ryan et al. | |
| 2007/0214133 A1 | 9/2007 | Liberty et al. | |
| 2007/0233603 A1 | 10/2007 | Schmidgall et al. | |
| 2007/0260492 A1* | 11/2007 | Feied | G06F 19/322 705/3 |
| 2007/0276858 A1 | 11/2007 | Cushman et al. | |
| 2007/0288262 A1 | 12/2007 | Sakaue et al. | |
| 2008/0013808 A1* | 1/2008 | Russo | G06K 9/00026 382/125 |
| 2008/0046292 A1* | 2/2008 | Myers | G06F 17/30557 705/3 |
| 2008/0082980 A1 | 4/2008 | Nessland et al. | |
| 2008/0091592 A1 | 4/2008 | Blackburn et al. | |
| 2008/0126264 A1 | 5/2008 | Tellefsen et al. | |
| 2008/0133436 A1 | 6/2008 | Di Profio | |
| 2008/0288292 A1 | 11/2008 | Bi et al. | |
| 2008/0295094 A1 | 11/2008 | Korupolu et al. | |
| 2008/0319983 A1 | 12/2008 | Meadows | |
| 2009/0083664 A1 | 3/2009 | Bay | |
| 2009/0125796 A1* | 5/2009 | Day | G06F 9/4443 715/219 |
| 2009/0192864 A1 | 7/2009 | Song et al. | |
| 2009/0198520 A1 | 8/2009 | Piovanetti-Perez | |
| 2009/0300054 A1 | 12/2009 | Fisher et al. | |
| 2009/0307104 A1 | 12/2009 | Weng | |
| 2009/0313045 A1 | 12/2009 | Boyce | |
| 2010/0076950 A1 | 3/2010 | Kenedy et al. | |
| 2010/0082620 A1 | 4/2010 | Jennings, III et al. | |
| 2010/0088108 A1 | 4/2010 | Machado | |
| 2010/0088119 A1 | 4/2010 | Tipirneni | |
| 2010/0138243 A1 | 6/2010 | Carroll | |
| 2010/0217973 A1* | 8/2010 | Kress | G06F 17/30 713/153 |
| 2010/0228721 A1* | 9/2010 | Mok | G06F 19/322 707/711 |
| 2010/0295674 A1 | 11/2010 | Hsieh et al. | |
| 2010/0332273 A1 | 12/2010 | Balasubramanian et al. | |
| 2011/0015947 A1 | 1/2011 | Erry et al. | |
| 2011/0047169 A1* | 2/2011 | Leighton | G06F 17/30675 707/756 |
| 2011/0055252 A1 | 3/2011 | Kapochunas et al. | |
| 2011/0071857 A1 | 3/2011 | Malov et al. | |
| 2011/0137672 A1 | 6/2011 | Adams et al. | |
| 2011/0218827 A1* | 9/2011 | Kenefick | G06Q 40/00 705/4 |
| 2011/0270625 A1 | 11/2011 | Pederson et al. | |
| 2012/0011029 A1 | 1/2012 | Thomas et al. | |
| 2012/0023107 A1* | 1/2012 | Nachnani | G06F 17/30303 707/748 |
| 2012/0035984 A1 | 2/2012 | Srinivasa et al. | |
| 2012/0078940 A1 | 3/2012 | Kolluri et al. | |
| 2012/0130736 A1 | 5/2012 | Dunston et al. | |
| 2012/0158429 A1 | 6/2012 | Murawski et al. | |
| 2012/0158750 A1 | 6/2012 | Faulkner et al. | |
| 2012/0173279 A1* | 7/2012 | Nessa | G06Q 10/063118 705/3 |
| 2012/0245958 A1 | 9/2012 | Lawrence et al. | |
| 2012/0246727 A1* | 9/2012 | Elovici | H04L 12/2602 726/23 |
| 2012/0290320 A1 | 11/2012 | Kurgan et al. | |
| 2012/0290564 A1* | 11/2012 | Mok | G06F 19/322 707/722 |
| 2013/0030827 A1 | 1/2013 | Snyder et al. | |
| 2013/0044749 A1 | 2/2013 | Eisner et al. | |
| 2013/0085769 A1 | 4/2013 | Jost et al. | |
| 2013/0138554 A1 | 5/2013 | Nikankn et al. | |
| 2013/0166552 A1 | 6/2013 | Rozenwald et al. | |
| 2013/0204940 A1 | 8/2013 | Kinsel et al. | |
| 2013/0304903 A1 | 11/2013 | Mick et al. | |
| 2013/0332194 A1* | 12/2013 | D'Auria | G16H 10/60 705/3 |
| 2014/0046931 A1* | 2/2014 | Mok | G06F 19/322 707/722 |
| 2014/0056243 A1 | 2/2014 | Pelletier et al. | |
| 2014/0059084 A1 | 2/2014 | Adams et al. | |
| 2014/0088981 A1 | 3/2014 | Momita | |
| 2014/0136233 A1 | 5/2014 | Atkinson et al. | |
| 2014/0222482 A1 | 8/2014 | Gautam et al. | |
| 2014/0244300 A1 | 8/2014 | Bess et al. | |
| 2014/0278491 A1 | 9/2014 | Weiss | |
| 2014/0358578 A1 | 12/2014 | Ptachcinski | |
| 2014/0358845 A1 | 12/2014 | Mundlapudi et al. | |
| 2015/0006558 A1* | 1/2015 | Leighton | G06F 17/30675 707/756 |
| 2015/0095056 A1* | 4/2015 | Ryan | G06Q 50/24 705/2 |
| 2015/0112696 A1 | 4/2015 | Kharraz Tavakol | |
| 2015/0142464 A1 | 5/2015 | Rusin et al. | |
| 2015/0199482 A1 | 7/2015 | Corbin et al. | |
| 2015/0332283 A1 | 11/2015 | Witchey | |
| 2016/0028552 A1 | 1/2016 | Spanos et al. | |
| 2016/0055205 A1 | 2/2016 | Jonathan et al. | |
| 2016/0253679 A1 | 9/2016 | Venkatraman et al. | |
| 2016/0328641 A1 | 11/2016 | Alsaud et al. | |
| 2017/0060856 A1* | 3/2017 | Turtle | G06F 17/30 |
| 2017/0091397 A1 | 3/2017 | Shah et al. | |
| 2017/0132621 A1 | 5/2017 | Miller et al. | |
| 2018/0082183 A1* | 3/2018 | Hertz | G06F 17/30675 |

OTHER PUBLICATIONS

Bhattacharya, Indrajit and Getoor, Lise, *Entity Resolution in Graphs*, Department of Computer Science, University of Maryland (2005) (21 pgs.).

Chen et al., *Adaptive Graphical Approach to Entity Resolution*, Jun. 18-23, 2007, Proceedings of the 7th ACM/IEEE-CS Joint Conference on Digital Libraries, pp. 204-213 (10 pgs.).

Christen, *Data Matching, Concepts and Techniques for Record Linkage, Entity Resolution, and Duplicate Detection*, © Springer-Verlag Berlin Heidelberg, 2012 (279 pgs.).

Cohen et al., *A Comparison of String Metrics for Matching Names and Records*, © 2003, American Association for Artificial Intelligence (www.aaai.org) (6 pgs.).

Coleman et al., *Medical Innovation—a diffusion study*; The Bobbs-Merrill Company, Inc., 1966 (248 pgs.).

(56) References Cited

OTHER PUBLICATIONS

Domingos et al., *Mining High-Speed Data Streams*, (2000) (10 pgs.).
Greenhalgh et al., *Diffusion of Innovations in Health Service Organisations—a systematic literature review*, Blackwell Publishing, 2005 (325 pgs.).
Jackson et al., *The Evolution of Social and Economic Networks*, Journal of Economic Theory 106, pp. 265-295, 2002 (31 pgs.).
Jackson, Matthew O., *Social and Economic Networks*, Princeton University Press, 2008 (509 pgs.).
Krempl et al., *Open Challenges for Data Stream Mining Research*, SIGKDD Explorations, vol. 16, Issue 1, Jun. 2014 (64 pgs.).
Rebuge, *Business Process Analysis in Healthcare Environments*, 2011, Ellsevier Ltd., pp. 99-116 (18 pgs.).
Wasserman et al., *Social Network Analysis: Methods and Applications*, Cambridge University Press; 1994 (434 pgs.).
White et al., *Algorithms for Estimating Relative Importance in Networks*, Proceedings of the Ninth ACM SIGKDD International Conference on Knowledge Discovery and Data Mining, 2003 (10 pgs.).
Webpage: New Health Care Electronic Transactions Standards Versions 5010, D.0, and 3.0, Jan. 2010 ICN 903192; http://www.cms.gov/Regulations-and-Guidance/HIPAA-Adminstrative-Simplification/Versions5010andD0/downloads/w5010BasicsFctCht.pdf (4 pgs.).
Webpage: U.S. Dept. of Health and Human Services, Guidance Regarding Methods for De-identification of Protected Health Information in Accordance with the Health Insurance Portability and Accountability Act (HIPAA) Privacy Rule, http://www.hhs.gov/ocr/privacy/hipaa/understanding/coveredentities/De-identification/guidance.html printed Oct. 15, 2015 (14 pgs.).
PCT International Search Report of PCT/US14/52768; dated Nov. 21, 2014; (2 pgs.).
PCT Written Opinion of the International Searching Authority of PCT/US14/52768; dated Nov. 21, 2014; (5 pgs.).
(MATHJAX) Naive Bayes Categorisation (with some help form Elasticsearch). Dec. 29, 2013. Blog post. Retrieved from the Internet. Retrieved from: https://blog.wtf.sg/2013/12/29/naive-bayes-categarisation-with-some-help-from-elasticsearch/. pp. 1-5; pp. 2, 5; (8 pgs.).
Lin et al., *A simplicial complex, a hypergraph, structure in the latent semantic space of document clustering*, © Elsevier, 2005 (26 pgs.).
Anonymous: "Oauth—Wikipedia", Sep. 23, 2013. Retrieved from the Internet URL:https://en.wikipedia.org/w/index.php?title+oAuth&oldid+574187532 (3 pages).
Version 5010 and D.O, Center for Medicare & Medicaid Services (2 pgs.).
Anonymous: "Oauth" Wikipedia—Retrieved from the Internet URL:https://en.wikipedia.org/wiki/Oauth (8 pgs.).

\* cited by examiner

```
{
    "_id" : ObjectId("526827bf230038612ef148e1"),
    "Provider Enumeration Date" : "05/23/2005",
    "Provider First Name" : "DAVID",
    "Provider Middle Name" : "A",
    "Provider Business Mailing Address Postal Code" : "688482168",
    "Provider Business Practice Location Address City Name" : "KEARNEY",
    "Provider Gender Code" : "M",
    "Provider Business Practice Location Address State Name" : "NE",
    "Provider Business Mailing Address Telephone Number" : "3088652512",
    "Provider Business Mailing Address Fax Number" : "3088652506",
    "Healthcare Provider Taxonomy Code_1" : "207X00000X",
    "Provider Business Practice Location Address Postal Code" : "688472944",
    "Last Update Date" : "07/08/2007",
    "Provider Business Practice Location Address Country Code (If outside US)" : "US",
    "Provider First Line Business Practice Location Address" : "3500 CENTRAL AVE",
    "Provider Last Name (Legal Name)" : "WIEBE",
    "Provider Credential Text" : "M.D.",
    "NPI" : "1679576722",
    "Provider Business Practice Location Address Telephone Number" : "3088652512",
    "Provider Business Mailing Address City Name" : "KEARNEY",
    "Provider Business Practice Location Address Fax Number" : "3088652506",
    "Provider Business Mailing Address State Name" : "NE",
    "Provider First Line Business Mailing Address" : "PO BOX 2168"
}
```

FIGURE 4

```
{
        "_id" : ObjectId("526827bf230038612ef148e1"),
        "address" : [
                {
                "address_lines" : [
                "PO BOX 2168"
                ],
                "city" : "KEARNEY",
                "country" : "US",
                "zipcode" : "688482168",
                "state" : "NE",
                "role" : "mailing"
                },
                {
                "address_lines" : [
                "3500 CENTRAL AVE"
                ],
                "city" : "KEARNEY",
                "country" : "US",
                "zipcode" : "688472944",
                "state" : "NE",
                "role" : "practice"
        }
        ],
        "taxonomy_codes" : [
        "207X00000X"
        ],
        "credential_text" : "M.D.",
        "mailing_fax" : "3088652506",
        "npi" : "1679576722",
        "practice_fax" : "3088652506",
        "last_update_date" : ISODate("2007-07-08T00:00:00Z"),
        "practice_phone" : "3088652512",
        "mailing_phone" : "3088652512",
        "name" : [
        {
                        "first_name" : "DAVID",
                        "last_name" : "WIEBE",
                        "middle_name" : "A"
        }
        ],
        "gender" : "M",
        "enumeration_date" : ISODate("2005-05-23T00:00:00Z")
}
```

FIGURE 5

```
{
        "_id" : ObjectId("5245af2a2300381f647152cf"),
        "matches" : [
                {
                        "_id" : ObjectId("52581aea2300386175e803c2"),
                        "collection" : "mapped_ama.denorm"
                },
                {
                        "_id" : ObjectId("52581aea2300386175e803c3"),
                        "collection" : "mapped_ama.denorm"
                },
                {
                        "_id" : ObjectId("52581aea2300386175e803c5"),
                        "collection" : "mapped_ama.denorm"
                },
                {
                        "_id" : ObjectId("52581aea2300386175e803c4"),
                        "collection" : "mapped_ama.denorm"
                }
        ],
        "collection" : "mapped_ama.ppd_quarterly_startup_dbl_denorm"
}
```

FIGURE 6

```
{
    u'name': [{'prov': [{'_id': ObjectId('5245ac7a2300381f646342be'),
                         u'source_collection': [u'ppd_quarterly_startup_dbl',
                                                u'ppd_quarterly_startup_dbl']}],
               'val': {u'first_name': u'MICHAEL',
                       u'full_name': u'MICHAEL ROBERT WRIGHT',
                       u'last_name': u'WRIGHT',
                       u'middle_name': u'ROBERT'}},
              {'prov': [{'_id': ObjectId('52419f8c2300383db8f125c0'),
                         u'source_collection': [u'state_licensures_TX',
                                                u'state_licensures']},
                        {'_id': ObjectId('52419f8c2300383db8f125c1'),
                         u'source_collection': [u'state_licensures_TX',
                                                u'state_licensures']}],
               'val': {u'first_name': u'MICHAEL ROBERT',
                       u'last_name': u'WRIGHT'}},
              {'prov': [{'_id': ObjectId('52409772230038235a5c8d14'),
                         u'source_collection': [u'state_licensure_KS',
                                                u'state_licensures']}],
               'val': {u'first_name': u'Michael', u'last_name': u'Wright'}}],
    ...
}
```

FIGURE 7

```
{
    u'name': [{'prov': [{'_id': ObjectId('5245ac7a2300381f646342be'),
                        u'source_collection': [u'ppd_quarterly_startup_dbl',
                                               u'ppd_quarterly_startup_dbl']}],
               'score': '0.66',
               'val': {u'first_name': u'MICHAEL',
                       u'full_name': u'MICHAEL ROBERT WRIGHT',
                       u'last_name': u'WRIGHT',
                       u'middle_name': u'ROBERT'}},
              {'prov': [{'_id': ObjectId('52419f8c2300383db8f125c0'),
                         u'source_collection': [u'state_licensures_TX',
                                                u'state_licensures']},
                        {'_id': ObjectId('52419f8c2300383db8f125c1'),
                         u'source_collection': [u'state_licensures_TX',
                                                u'state_licensures']}],
               'score': '0.55',
               'val': {u'first_name': u'MICHAEL ROBERT',
                       u'last_name': u'WRIGHT'}},
              {'prov': [{'_id': ObjectId('52409772230038235a5c8d14'),
                         u'source_collection': [u'state_licensure_KS',
                                                u'state_licensures']}],
               'score': '0.27',
               'val': {u'first_name': u'Michael', u'last_name': u'Wright'}}],
    ...
}
```

FIGURE 8

SYSTEM AND METHOD FOR DYNAMIC DOCUMENT MATCHING AND MERGING

PRIORITY CLAIMS/RELATED APPLICATIONS

This application claims the benefit of and priority to, under 35 USC 119(e) to U.S. Provisional Patent Application Ser. No. 61/929,787 filed Jan. 21, 2014 and entitled "System and Method for Dynamic Document Matching and Merging", the entirety of which is incorporated herein by reference.

FIELD

The disclosure relates generally to a system and method for matching and merging disparate documents.

BACKGROUND

Data about an entity, such as a subject, company, idea or the like, may be stored in a plurality of disparate data sources. In order to be able to assemble the data about the entity from the disparate sources into a single data store, it is necessary to try to gather the various data from the various data sources and then determine a way to combine the data from the disparate data sources for the particular entity into the single data store.

In the healthcare industry, information/data about each healthcare provider, such as a doctor, a therapist, a nurse, a hospital, a medical practice and the like, may be stored in a plurality of disparate data sources. The information/data about the healthcare provider may include, for example, reviews, directions, rates and the like. The disparate data sources for the data/information for the healthcare provider may include publicly available Centers for Medicare and Medicaid Services' (CMS) National Plan and Provider Enumeration System (NPPES) data to privately curated and licensed data from the American Medical Association (AMA), among others.

The issues that must be confronted in order to successfully integrate the data from these various data sources into a single data store may include:
- While the provider documents are structured, the available data fields are heterogeneous across data sources.
- There is no strong identifier linking provider documents across data sources. Even a provider's name may be suspect for a number of reasons:
  - Names may be legally changed
  - Informal variations (i.e., nicknames)
  - Misspellings due to human error
  - Inconsistent localization from non-Roman alphabets
  - Multiple providers with the same name
- No single data source can be trusted as authoritative, as there is no central mechanism in place to update each concerned organization as provider information changes over time.
- As there is no central mechanism for updating provider information, the data available from NPPES, AMA and others invariably become out of sync even among the commonly available data fields.
- While the data from NPPES, AMA and others provide a top-level view of their own provider directories, they too have combined data from potentially thousands of lower level sources, and errors may have propagated through their own system.

There are more than one million individual healthcare providers in the United States, and manual curation and inspection of all providers' data is not feasible.

Thus, it is desirable to provide a system and method for dynamic data identification and combining so that, for example, data from disparate data sources for a healthcare provider may be combined into a single data store.

BRIEF DESCRIPTION OF THE DRAWINGS

FIG. 4 illustrates an example of a source provider document that may be matched and merged using the process shown in FIG. 1;

FIG. 5 illustrates an example of an aligned and structured provider document that may be matched and merged using the process shown in FIG. 1;

FIG. 6 illustrates an example of a match set;

FIG. 7 is an example of an excerpt from a merged document with provenance generated by the method in FIG. 1; and FIG. 8 is an example of an excerpt from a merged document with ranked values and provenance generated by the method in FIG. 1.

DETAILED DESCRIPTION OF ONE OR MORE EMBODIMENTS

Figure 1:
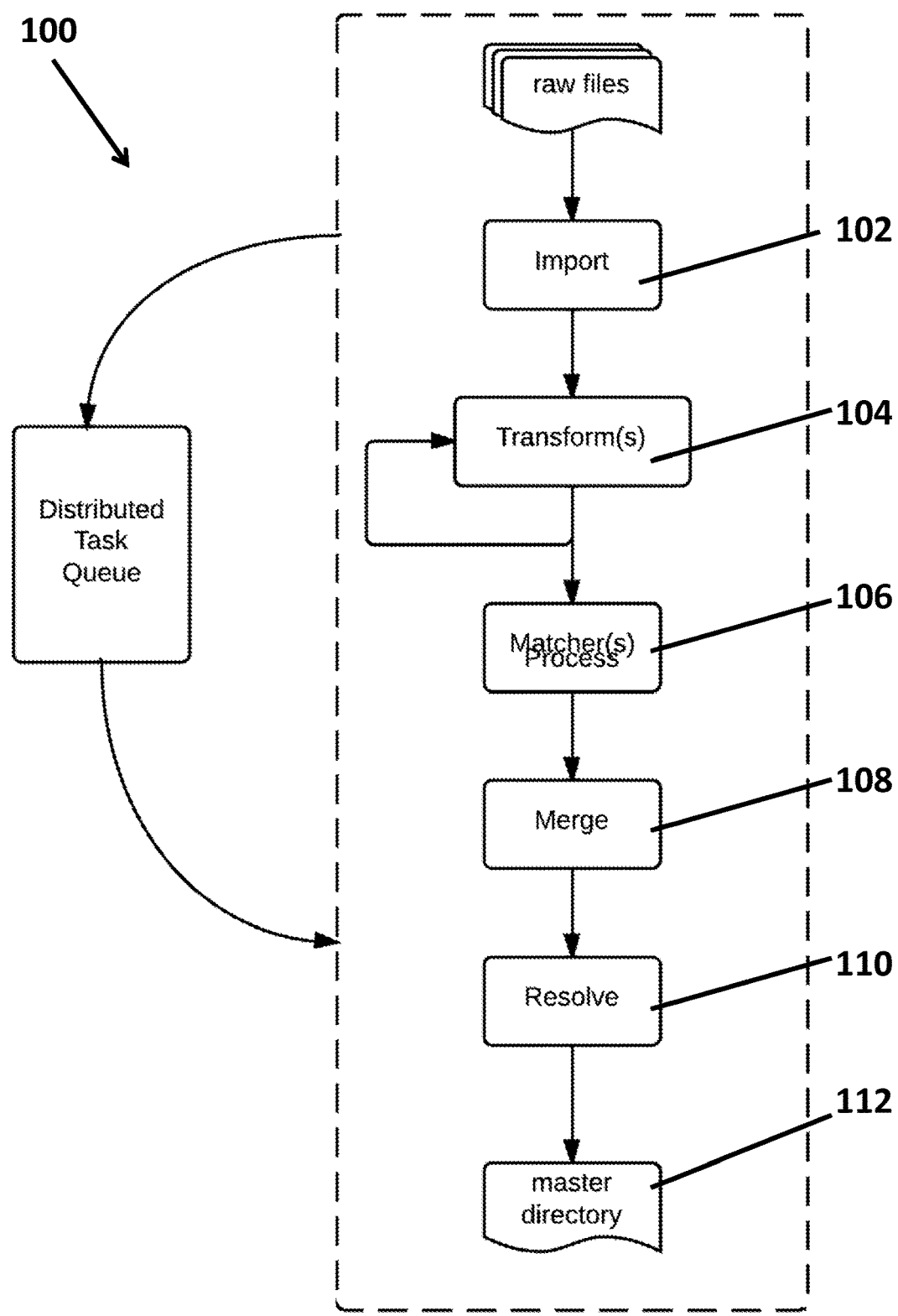
FIG. 1 is a top level process flow for a method for matching and merging documents.

The disclosure is particularly applicable to a healthcare system in which healthcare provider data is matched and merged and it is in this context that the disclosure will be described. It will be appreciated, however, that the system and method has greater utility since the system and method may be used with any type of entity for which it is desirable to be able to match and merge data about the entity from disparate data sources. Furthermore, the system and method may be used in any industry for which it is desirable to be able to match and merge data about the entity from disparate data sources. For purposes of this disclosure, an entity may be a subject, an idea, a professional, a person, a corporation, a business entity and the like.

In an example healthcare embodiment, a healthcare system may have a goal of providing healthcare pricing transparency and connecting consumers directly to healthcare providers. To provide that healthcare pricing transparency, the healthcare system needs to maintain a comprehensive and up-to-date directory of healthcare providers. In order to build this provider directory, data are combined from disparate sources ranging from the publicly available Centers for Medicare and Medicaid Services' (CMS) National Plan and Provider Enumeration System (NPPES) data to privately curated and licensed data from the American Medical Association (AMA), among others. These data take the form of structured records on a per-provider basis, referred to herein as provider documents.

The system and method provide a computational process to match provider documents from disparate sources which refer to the same provider and merge those documents into a single comprehensive view while taking into account the relative trustworthiness of the data sources for each available data field. The generated single comprehensive view facilitates a more accurate services purchasing and recommendation experience for the healthcare consumer as well as the practitioner in the application domain. The ability to dynamically match disparate data sources with data hygiene metric is crucial in evaluating the behaviors and ratings for ranking practitioners that will be listed in a marketplace of the healthcare system. This improved matching model further facilitates a faceted search paradigm much like one would search for a camera purchase at an internet marketplace site.

The system may include one or more of the following components:
- a plurality of provider document matcher algorithms.
- a method for providing human verification feedback on a random sampling of match algorithm results.
- a statistical model built from the human verification feedback loop, used to select and combine result match sets from the match algorithms.
- a method to merge the original provider documents contained within each selected match set, maintaining provenance for each field/value pair in the merged document.
- a method to resolve conflicting values for available fields in the merged provider documents.
- an Extract Transform and Load (ETL) method for distributing these processes via a transform pipeline that allows for optimized and distributed processing of the disparate data sets
- a distributed process that utilizes a message queuing and enterprise service bus to dynamically process the ETL information.

FIG. 1 is a top level process flow for a method 100 for matching and merging documents. The system that implements the process flow is designed to allow for multiple matcher algorithms in order to take advantage of the relative strengths of each algorithm while compensating for their individual weaknesses. For instance, a strict matcher may utilize statistically significant combinations of biographic identifiers such as each component of a person's full name as well as birth date and birth place, which would produce few false positives in the search space yet would produce a false negative if an actual matching document in the search space lacked any component of the full name (e.g., middle name) or the birth information. Conversely, a loose matcher that allows for variations in a person's name (e.g., nicknames) would be more successful in reducing false negatives but would produce far more false positives.

For example, the system may use Bayesian Identity Resolution in which comparators and weight ranges are specified for a subset of the fields in the documents which are determined to be the best features for determining matches. When document pairs are evaluated, each field in the documents are compared using the specified comparator and the result is scaled to the specified weight range resulting in a weighted match score for the field. These weighted field match scores are combined using Bayes' theorem to provide an overall match score for the two documents. If this document match score is above a designated threshold than the two documents are considered to be a match, otherwise they are considered not to match.

As another example, the system may use ElasticSearch. ElasticSearch is a distributed, RESTful, free/open source search server based on Apache Lucene, an open source information retrieval software library. To perform document matching using Elasticsearch, a collection of documents is first "indexed" using the Elasticsearch API. Then a collection of documents is iterated upon, constructing a precise boolean query based on select fields from the iterated document. If the necessary fields are present in this "query" document, the query is issued against the Elasticsearch index, and results indicate a positive match which is saved into results collection. For collection deduplication the iterated collection may be the same collection that was indexed. Alternatively for record "linkage" an entirely different collection may be iterated upon.

Prior to running the ensemble of matcher algorithms, each of the source documents (raw files in FIG. 1) are imported 102 and assigned a unique identifier. Those identifiers remain with the documents as they are transformed 104, for example, to align vocabulary (i.e., field names) where appropriate, and to de-normalize the logical data structures within the documents (e.g., grouping components of a mailing address within an 'address' sub-document). FIGS. 4 and 5 show an example of a source provider document and its aligned/structured version, respectively.

Following the initial data cleansing, each matcher algorithm may be run (matcher processes 106) against the entire set of N provider documents from all sources (our search space). This may be viewed as a sequence of queries using M canonical data source documents as the query documents for which we wish to find corresponding matches in the search space, resulting in M match sets (see FIG. 6 for an example of a match set). Ultimately the matched documents will be folded into the canonical documents to provide an updated, unified view of the data. An alternative embodiment may run the matcher algorithms using the N search space documents as the query documents to perform de-duplication, but for the purposes of folding multiple sources of provider documents into the comprehensive directory we use the same set of query documents across all matcher instantiations.

The generated match sets do not contain the actual matching documents, but rather contain references to the matching documents' storage locations and unique identifiers as shown in FIG. 6. The unique identifiers refer to those assigned to the matching documents during initial import 102. Additionally the match sets have associated provenance metadata for the matcher algorithms by which they are produced, including the algorithm's identifier and the parameters specific to its instantiation. The matcher provenance is used to differentiate match set results by the statistical model that selects and combines the match sets.

A statistical model may be constructed using the results of human evaluation of a random sample of match sets produced by the matcher ensemble. The human evaluator may be presented with the query document and each pair-wise combination with the matching documents represented by a match set. The evaluator determines whether the two documents refer to the same provider, and the determination (or score) is stored for future reference. It is possible that a match set contains both correct and incorrect matches.

The collection of match scores forms the basis of the training data for building the statistical model, along with the feature vector for each document in the training data. For example, an example of the feature vector may be:

```
{
    query_source: "ppd_quarterly_startup",
    match_source: "nppes_npi",
    actual_match: True,
    field_distances: {
        "address.address_lines": 0,
        "address.city": 0,
        "address.zipcode": 4,
```

-continued

```
        "address.state": 0,
        "address.country": 0,
        "name.first_name": 0,
        "name.last_name": 0,
        "name.middle_name": 5,
        "gender": 0,
        "practice_phone": 0
    }
}
```

A sparse representation of the feature vector for one record in the training data set. This shows that a provider document in the ppd_quarterly_startup source was correctly matched with a provider document in the nppes_npi source. The presence of a field name in the field_distances data structure indicates that the field was present in both documents, and the associated number is the Levenshtein distance between the field values in the two documents. These field names are based on the example in FIG. 5, which is the data from FIG. 4 with transformed vocabulary.

These features (and all the features of the entire training data set) are the predictors for the Bayesian classifier.

The feature vectors may be comprised of individual data points such as document sources, available document fields, similarity of fields between query and matching documents. Bayesian inference may then be used to determine whether a proposed match as presented in a match set is predicted to be valid. By taking each match in a match set into consideration individually it is possible to accept or reject subsets. As the same set of query documents is used across matchers, the accepted matches for each query document across all matchers are able to be combined into complete match sets.

At this point in the process, the combined match sets are still represented by references to the documents of interest. The next step is to merge the referenced documents (108) (including both the query and match documents) into a single document, with values from all fields present in each. Provenance is maintained for all field/value combinations to track their origins. New unique identifiers are assigned to the resulting merged documents, even if the merge resulted from a singleton match set.

The merged documents may have conflicting values for any given field. The process may thus have a resolve process 110 to resolve such conflicts and rank the values according to confidence in each value's correctness. The resolve process 110 may be accomplished using a combination of heuristics including majority rule (value support), predetermined confidence for data sources (e.g., trusting state medical boards for practitioner licensing data), or once again a statistical model built from human feedback. For example, a "majority rule" resolver would determine the most consistent data value for a given field based on which value for the given data filed that occurs most often. At least three sources would be needed to determine a "winner". For the merged document in FIG. 8, this resolver would score the 'name' field from ppd_quarterly_startup_dbl and state_licensures_TX sources as 0.66, since those two (first_name, middle_name, last_name) tuples out of the three were identical. The state_licensure_KS would score 0.33, since it only occurred once out of the three. In this case the winner could either be the ppd_quarterly_startup or state_licensure_TX since their scores are identical.

The canonical documents, which were used as the query documents by the matcher ensemble, now have the field/value combinations from matching documents folded in, along with rankings for each. The consumer of these new documents, as outputted by the system, may choose to utilize the ranked values as appropriate, the simplest case being only to take the highest ranking values. Alternately, the combined documents with ranked values may be preserved as is for display in a faceted browsing system for exploration by the user. The combined documents, in the healthcare example scenario, may be stored in a master directory 112 for healthcare providers.

Figure 2:
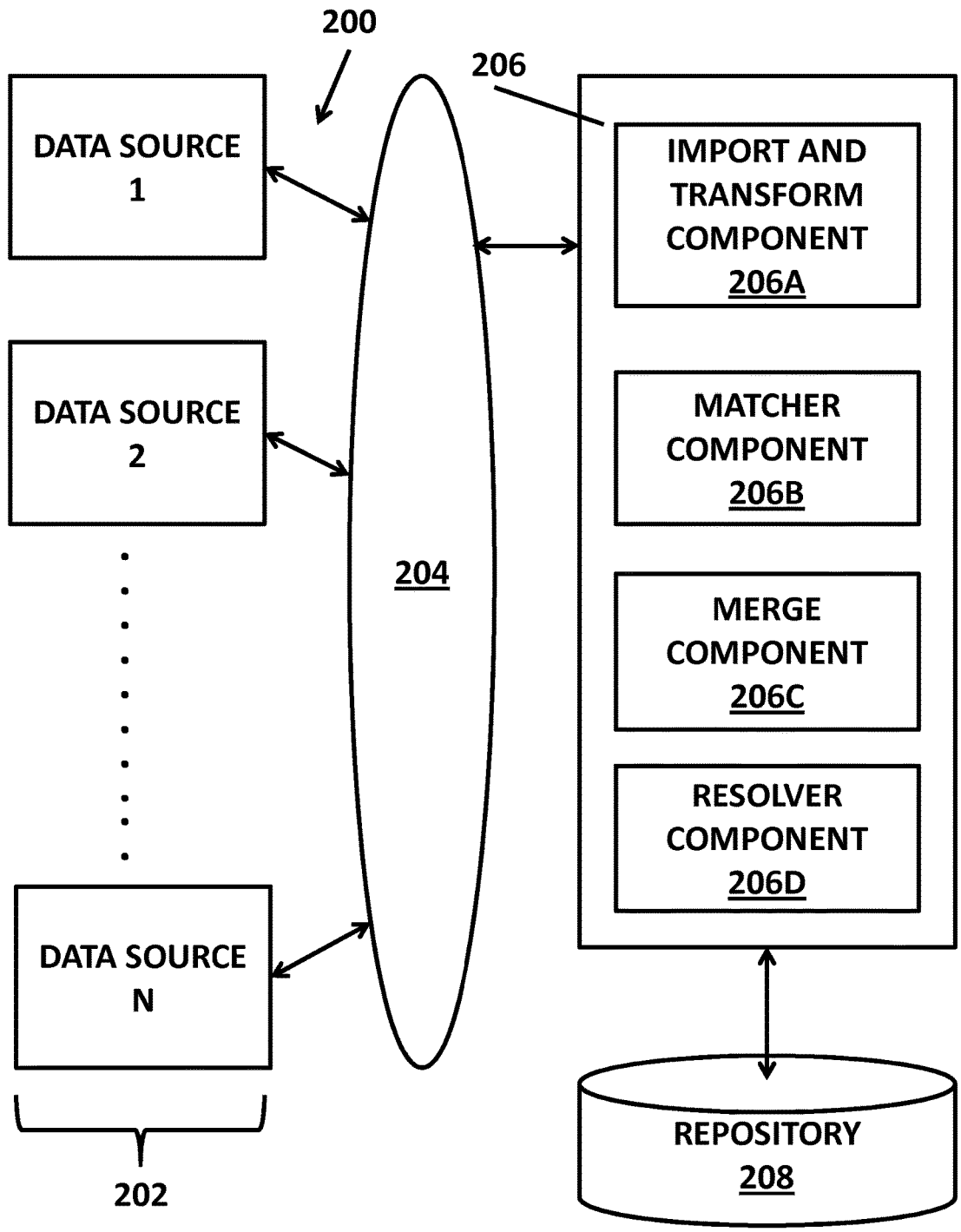
FIG. 2 is an example of an implementation of a system for matching and merging documents.
Figure 3:
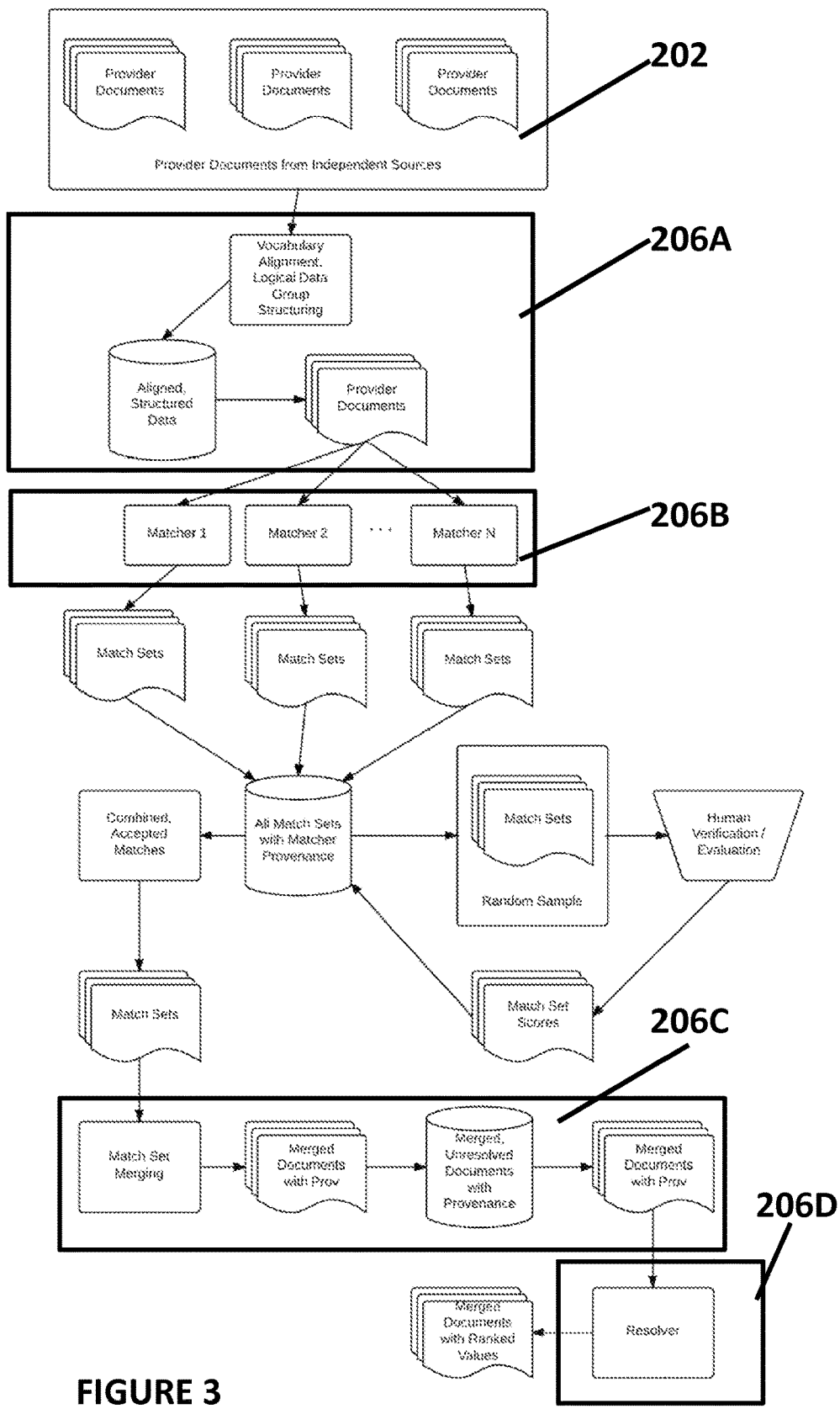
FIG. 3 illustrates more details of the system shown in FIG. 2.

FIG. 2 is an example of an implementation of a system 200 for matching and merging documents and FIG. 3 illustrates more details of the system shown in FIG. 2. The system 200 may have one or more data sources 202, such as data source 1, data source 2, . . . , data source N as shown in FIG. 2, from which data about a particular entity may be pulled. In the healthcare example scenario, the entity may be a healthcare provider and the one or more data sources may be publicly available Centers for Medicare and Medicaid Services' (CMS) National Plan and Provider Enumeration System (NPPES) data and/or privately curated and licensed data from the American Medical Association (AMA). In the healthcare example scenario, the data in the data sources may take the form of structured records on a per-provider basis, referred to herein as provider documents.

The one or more data sources 202 may be geographically dispersed or co-located, but each may have a connection to a communication path 204 and may be implemented as a software or hardware based data store or database. The one or more data sources 202 may have data obtained from them over a communication path 204 by a backend unit 206. The communication path 204 may be any wired or wireless network that allows the backend unit 206 to collect data from the data sources, such as the Internet, a wireless data or computer network, a wired data network and the like.

The backend unit 206 may be implemented using one or more cloud computing resources or one or more server computing resources such as at least a processor and a memory. The backend unit may further comprise a plurality of components wherein each component performs one or more processes to implement the matching and merging functionality of the system. Each component may be a plurality of lines of computer code that may be resident in the memory of the cloud computing resources or one or more server computing resources and executed by the processor of the cloud computing resources or one or more server computing resources. Alternatively, each component may be a piece of hardware that implements the operations and processes described. For example, each component may be a programmable logic device, a microprocessor or microcontroller with microcode, an application specific integrated circuit and the like.

The components of the backend unit 206 may include an import and transform component 206A that may perform the import and transform processes 102,104 described above with reference to FIG. 1 and a matcher component 206B that may house the one or more matcher algorithms described above that perform the matching process 106 in FIG. 1. The components of the backend unit 206 may further include a merge component 206C that may perform the merge process 110 and a resolver component 206D that may perform the resolve process 112 described above with reference to FIG. 1.

In addition to the components, the backend unit 206 may be coupled to a repository 208 that may store the match sets, the merged documents and the merged documents with rank values. In the healthcare example scenario, the repository 208 may also store the healthcare provider directory based on the merged documents with rank values.

FIG. 3 illustrates the system when used for a healthcare example scenario in which healthcare provider data is generated from the disparate data sources. Thus, as shown in FIG. 3, each disparate data source may have one or more provider documents that contain data about a particular healthcare provider. Similar to the process shown in FIG. 1, the provider documents may be import and transformed into aligned, structured provider data that may be stored in the repository 208 shown in FIG. 2. As described above, the aligned, structured provider data documents may be matched using one or more matchers and each matcher generates a match set (an example of which is shown in FIG. 6.) The match sets for each matcher (with the provenance) may be stored in the repository and a human verification process may be performed as described above.

Once the human review process is completed, the combined, accepted matches and their match sets may be merged together with the provenance from the match sets. An example of an excerpt from such a document is shown in FIG. 7. Those merged document with provenance may be unresolved and those documents may be input to the resolver 206D which then generates merged documents with ranked values. An example of an excerpt from a merged document with ranked values provenance is shown in FIG. 8.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A system for matching and merging data for an entity from disparate data sources, comprising:
one or more data sources for disparate sources, each data source having a raw file about an entity, each raw file having a plurality of data fields and each field has a value associated with the entity;
a computer system having a processor, the computer system coupled to each of the one or more data sources;
the processor of the computer system being configured to receive the one or more raw files about the entity from the one or more data sources;
the processor of the computer system being configured to perform each of a plurality of matching processes against each of the one or more raw files about the entity to generate a match set for each raw file matched with one of the plurality of matching processes based on results from each of the plurality of matching processes with each of the raw files wherein the match set for each raw file matched by each one of the plurality of matching processes a reference to a document storage location of the raw file, a unique identifier for the raw file and provenance metadata for the one matching process including an identifier of the matching process and parameters associated with the matching process;
the processor of the computer system being configured to merge the one or more raw files represented into a merged document that has the at least one matched data field in each of the one or more raw files; and
the processor of the computer system being configured to identify conflicting values in each data field of the merged document.

2. The system of claim 1, wherein the processor is configured to transform, before performing the plurality of matching processes, the one or more raw files to initial data cleanse the one or more raw files and generate one or more transformed files about the entity.

3. The system of claim 1, wherein the processor is configured to rank each conflicting value for a data field based on a confidence of a correctness of each conflicting value.

4. The system of claim 1, wherein the processor is configured to perform a sequence of queries on the one or more raw files, wherein each query generates the match set.

5. The system of claim 1, wherein the processor is configured to use a Bayesian identity resolution process and uses an ElasticSearch process.

6. The system of claim 1, wherein the entity is one of a healthcare provider, subject, an idea, a professional, a person, a corporation and a business entity.

7. The system of claim 1, wherein the entity is a healthcare provider and the one or more raw files are a Centers for Medicare and Medicaid Services' (CMS) National Plan and Provider Enumeration System (NPPES) data file and an American Medical Association (AMA) file.

8. A method for matching and merging data for an entity from disparate data sources, comprising:
receiving, by a computer system, one or more raw files from disparate sources about an entity, each raw file having a plurality of data fields and each field has a value associated with the entity;
performing, by the computer system, each of a plurality of matching processes against each of the one or more raw files about the entity to generate a match set for each raw file matched with one of the plurality of matching processes based on results from each of the plurality of matching processes with each of the raw files wherein the match set for each raw file matched by each one of the plurality of matching processes a reference to a document storage location of the raw file, a unique identifier for the raw file and provenance metadata for the one matching process including an identifier of the matching process and parameters associated with the matching process;
merging, by the computer system, the one or more raw files represented into a merged document that has the at least one matched data field in each of the one or more raw files; and
identifying, by the computer system, conflicting values in each data field of the merged document.

9. The method of claim 8 further comprising transforming, by the computer system before performing the plurality of matching processes, the one or more raw files to initial data cleanse the one or more raw files and generate one or more transformed files about the entity.

10. The method of claim 8, wherein identifying the conflicting values further comprises ranking each conflicting value for a data field based on a confidence of a correctness of each conflicting value.

11. The method of claim 8, wherein performing the plurality of matching processes further comprises performing a sequence of queries on the one or more raw files, wherein each query generates the match set.

12. The method of claim 11, wherein the match set for a particular raw file has a reference to a storage location of the particular raw file and a unique identifier.

13. The method of claim 8, wherein performing the plurality of matching processes further comprises using a Bayesian identity resolution process and using an ElasticSearch process.

14. The method of claim 8, wherein the entity is one of a healthcare provider, subject, an idea, a professional, a person, a corporation and a business entity.

15. The method of claim 8, wherein the entity is a healthcare provider and the one or more raw files are a Centers for Medicare and Medicaid Services' (CMS) National Plan and Provider Enumeration System (NPPES) data file and an American Medical Association (AMA) file.

16. A system for matching and merging data for an entity from disparate data sources, comprising:
   one or more data sources for disparate sources, each data source having a raw file about an entity, each raw file having a plurality of data fields and each field has a value associated with the entity;
   a computer system having a processor, the computer system coupled to each of the one or more data sources;
   the processor of the computer system being configured to perform each of a plurality of matching processes against each of the one or more raw files about the entity to generate a match set for each raw file matched with one of the plurality of matching processes wherein the match set for each raw file matched by each one of the plurality of matching processes a reference to a document storage location of the raw file, a unique identifier for the raw file and provenance metadata for the one matching process including an identifier of the matching process and parameters associated with the matching process, the plurality of matching processes including a strict matcher process that utilizes statistically significant combinations of biographic identifiers including each component of a person's full name, a birth date and a birth place and a loose matcher process that allows for a variation in a person's name;
   the processor of the computer system being configured to merge the one or more raw files represented into a merged document that has the at least one matched data field in each of the one or more raw files; and
   the processor of the computer system being configured to identify conflicting values in each data field of the merged document.

17. A method for matching and merging data for an entity from disparate data sources, comprising:
   receiving, by a computer system, one or more raw files from disparate sources about an entity, each raw file having a plurality of data fields and each field has a value associated with the entity;
   performing, by the computer system, a plurality of matching processes against the one or more raw files about the entity to generate a match set for each raw file matched with one of the plurality of matching processes wherein the match set for each raw file matched by each one of the plurality of matching processes a reference to a document storage location of the raw file, a unique identifier for the raw file and provenance metadata for the one matching process including an identifier of the matching process and parameters associated with the matching process, the plurality of matching processes including a strict matcher process that utilizes statistically significant combinations of biographic identifiers including each component of a person's full name, a birth date and a birth place and a loose matcher process that allows for a variation in a person's name;
   merging, by the computer system, the one or more raw files represented into a merged document that has the at least one matched data field in each of the one or more raw files; and
   identifying, by the computer system, conflicting values in each data field of the merged document.

* * * * *